United States Patent
Kaartinen et al.

(10) Patent No.: US 7,608,464 B2
(45) Date of Patent: Oct. 27, 2009

(54) METHOD FOR USE IN TESTING OF LIQUID SAMPLES, A TEST UNIT UTILIZING THE METHOD AND A SYSTEM COMPRISING SUCH TEST UNITS

(76) Inventors: Niilo Kaartinen, Vuolahti, FIN-21620 Kuusisto (FI); Timo Kaartinen, Paraistentie 19 C 36, FIN-00280 Helsinki (FI)

(*) Notice: Subject to any disclaimer, the term of this patent is extended or adjusted under 35 U.S.C. 154(b) by 1075 days.

(21) Appl. No.: 10/467,022

(22) PCT Filed: Jan. 31, 2002

(86) PCT No.: PCT/FI02/00073

§ 371 (c)(1),
(2), (4) Date: Jan. 22, 2004

(87) PCT Pub. No.: WO02/061395

PCT Pub. Date: Aug. 8, 2002

(65) Prior Publication Data

US 2004/0115829 A1   Jun. 17, 2004

(30) Foreign Application Priority Data

Feb. 1, 2001   (FI) .................................. 20010190

(51) Int. Cl.
*G01N 1/10* (2006.01)
*E03B 1/00* (2006.01)
*C12Q 1/68* (2006.01)
*F16K 51/00* (2006.01)

(52) U.S. Cl. .............................. 436/180; 137/3; 422/50; 251/142

(58) Field of Classification Search ................. 436/180; 137/3; 422/50; 251/142
See application file for complete search history.

(56) References Cited

U.S. PATENT DOCUMENTS

| 4,588,554 | A |   | 5/1986 | Kaartinen et al. |
| 5,311,896 | A | * | 5/1994 | Kaartinen ................. 137/15.01 |
| 5,638,986 | A | * | 6/1997 | Tuominen et al. ............... 222/1 |
| 5,863,801 | A | * | 1/1999 | Southgate et al. ............. 436/63 |
| 6,055,487 | A |   | 4/2000 | Margery et al. |

FOREIGN PATENT DOCUMENTS

| EP |   | 0800073 |    | 10/1997 |
| EP |   | 1046823 | A2 * | 3/2000 |
| GB |   | 2294761 |    | 5/1996 |
| WO | WO 88/00347 | A |    | 1/1988 |

* cited by examiner

*Primary Examiner*—Jill Warden
*Assistant Examiner*—Lore Jarrett
(74) *Attorney, Agent, or Firm*—Ware, Fressola, Van Der Sluys & Adolphson, LLP

(57) ABSTRACT

Diagnostic analyses of medical specimens or analyses of samples taken from industrial processes, waste treatment or the environment are made based on hydraulic dosage of liquids, in which a dosage space (8) of limited volume included in the test unit is filled with the medium needed in the test by means of a liquid actuator, such as a bellows (18), the sample being combined with the medium by absorption into the dosage space with the aid of the actuator, purging a corresponding amount of medium from the space under the effect of suction. If necessary, one or more reactants required in the test are drawn into the dosage space (8) on the same principle. The quantitatively dosed liquids can then be mixed and transferred hydraulically into the incubation and/or detection spaces (25, 26) of the test unit with movements generated by the actuator (18). The system may include data transmission communications.

12 Claims, 2 Drawing Sheets

METHOD FOR USE IN TESTING OF LIQUID SAMPLES, A TEST UNIT UTILIZING THE METHOD AND A SYSTEM COMPRISING SUCH TEST UNITS

CROSS-REFERENCE TO RELATED APPLICATIONS

This is the national phase of International Application PCT/FI02/00073 filed Jan. 31, 2002 and claiming priority from Finnish application FI-20010190 filed on Feb. 1, 2001.

BACKGROUND OF THE INVENTION

1. Technical Field

The present invention relates to the testing of liquid samples. More specifically, the invention relates to a method for combining liquids for testing a liquid sample, the sample to be tested being combined quantitatively with a liquid medium. In addition, the invention relates to a test unit utilizing said method, and to a system including a plurality of such test units.

2. Discussion of Related Art

The invention is mainly implemented in the field of clinical chemistry, i.e. in analyses of medical specimens from patients for diagnostic purposes. A second central field of application relates to the analyses of samples from industrial processes, waste treatment and the environment.

Chemical tests are nowadays conducted in laboratories by means of analyzers, which are mechanized high-speed dispensing robots, whose operation is based on the transfer of liquids between open vessels. Such analyzers draw the samples to be tested and the reagents required for the tests from open tubes or containers into pipettes, transfer them by pipette suction into measuring filter troughs, perform mixing, and after the reaction, determine a parameter yielding the measurement result. The analyzer operation is controlled by measurements performed accordingly on reference samples with known contents.

Current analyzers have the benefit of high capacity, large test range and easy test variation. On the other hand, they have shortcomings relating especially to the open sample and reagent vessels and filter troughs and to the liquids being transferred by pipette suction between the vessels. Open vessels impair the conservation of liquids and expose the liquids to microbiological or similar contaminations. At the pipette suction stage, small air bubbles tend to be drawn alongside with the liquids, the air bubbles causing a corresponding volume error in a liquid batch that has been quantitatively dosed. At the injecting stage, again, a liquid droplet may occasionally remain at the pipette end under the effect of surface tension and thus be excluded from the analysis and result in a dosage error.

In current analyzers, there have been attempts to compensate for these errors caused by inexact pipette suction by using sufficiently great liquid volumes of tens to hundreds of microliters for minor air bubbles or any last liquid droplet remaining at the pipette end not to have any practical impact in terms of the quantitative result of the tests. However, as a result of this, the operational components of the analyzer, i.e. sample tubes, reagent containers and measurement filter troughs need to be given unnecessarily large dimensions in view of the actual test reaction, and also reagent consumption will be high. For these reasons and for the operational versatility required, current analyzers are typically large apparatuses of the size of a desk approximately, requiring professional staff for use and entailing high costs of investment and operation.

DISCLOSURE OF INVENTION

The purpose of this invention is to provide a solution in which quantitative dosage and combination of liquids required for tests, especially of a liquid sample to be tested and a liquid medium, are performed in a new manner, which eliminates the prior art drawbacks described above. The method of the invention is characterized by the combination of liquids taking place in a dosage space of limited volume, which is connected to a liquid actuator and to an inlet equipped with an on/off valve for the sample to be tested, and by the dosage space being filled with a medium, after which the valve of the sample inlet is opened and a determined volume of medium is removed from the space with the actuator so that a corresponding amount of sample is drawn under the effect of exhaust suction from the inlet through the valve to the dosage space.

The method of the invention is substantially based on hydraulic liquid transfer and liquid association in a test apparatus comprising a dosage space and associated ducts, where the liquids are brought into direct mutual contact and where on/off valves define the dosed liquid volumes without dosage errors caused by surface tension. Dosage is thus more accurate and allows a smaller-sized test apparatus and also smaller amounts of substance, reducing the costs of analysis. Hydraulic dosage is less susceptible to air bubbles entering liquids at the stages of dosage and association, and in addition, the test apparatus can be equipped with a suitable sensor, allowing the liquid movements to be monitored in the dosage space and the ducts. A pressure sensor, for instance, allows an air bubble accompanying the liquid to be detected and to be considered in the evaluation of the test result, or, if possible, the dosage may be repeated in order to obtain a liquid batch free of air bubbles. The feature of monitoring dosage with a sensor is a substantial advantage in automated, programmed dosage, for which hydraulic liquid transfer is particularly suitable.

The hydraulic liquid transfer and combination of the invention also have the advantage of the dosage space and the related ducts being easy to clean with cleaning fluid or drying air led through them. Since hydraulic dosage, unlike conventional liquid transfer by pipettes between open vessels, takes place in sealed spaces, the risk of contamination caused by external effects is reduced in the invention.

For liquids to be dosed and combined in the desired quantitative ratios, the liquid actuators must provide adequate precision. The higher the precision of repeated movements produced by the actuator, the better the quantitative dosage of the invention. An actuator that is accurate and thus advantageous for the method of the invention is a liquid-filled bellows, as described in connection with pipette dosage in U.S. Pat. No. 5,638,986. A bellows does not wear in use and the dosage precision provided allows for very small quantities of substances in tests.

In a typical chemical test of a liquid sample, the medium acts as a support and a diluent, with which one or more reagents reacting with the sample are associated besides the sample, the result of the test reaction or its absence forming the test result. In accordance with the invention, liquid dosage for such tests takes place in an apparatus, in which a plurality of inlets equipped with an on/off valve have been connected to the dosage space, each sample and also each reagent placed in advance in the apparatus having an inlet of their own. Liquids are associated by absorption not only of the sample to be tested but also one or more fluid reagents one by one from the inlets, so that a volume of medium corresponding to the specific drawn liquid volume is removed from the dosage space each time.

For exhaust suction to remove only medium from the dosage space and not sample or reagent dosed into the space at the preceding suction stage, the dosage space preferably comprises a narrow, elongated duct, which is connected to the liquid actuator by its end. A dosage space shaped in this manner prevents liquids from being mixed in an undesired way at successive suction stages of the dosage. Preferably, the entire dosage space is formed as an elongated duct connected by its end to an actuator and with sample and reagent inlets connected to different points of the duct, so that the sample and one or more reagents are drawn into the dosage space in succession before the ultimate stage of mixing by various means. This operation can be performed e.g. by reciprocating suction and expulsion movements generated by the actuator at the stage of removing the dosed liquids from the dosage space, with a view to complete the reaction and detect the reaction result, for instance.

After the liquids have been associated in the dosage space in the desired quantified specific ratios, air can advantageously be used as a buffer for forwarding the liquid from the dosage space. The air buffer isolates previously dosed and mutually associated liquids from other liquids, so that admixture with other liquids is not allowed to affect the reaction and the test result.

The test apparatus of the invention using the method described above, referred to as test unit below, is characterized by comprising a liquid dosage space with confined volume, an inlet for liquid medium connected to the dosage space, an inlet for liquid sample to be tested connected to the dosage space, one or more storage spaces for reagents reacting with the sample, each of which communicates through a flow channel with the dosage space, for removing liquids dosed into the flow channel from the dosage space, each of said inlets and flow channels being equipped with an on/off valve for flow control, a liquid actuator, and a detector for detecting the reaction result for test result determination.

Depending on the tests to be conducted, the test unit of the invention can optionally include one or more incubation spaces, in which combined liquids can be conserved over the period required for the test reaction while controlling the temperature if necessary, a detection space equipped with a detector for detecting the reaction result, and a sensor, such as a pressure sensor or a temperature sensor, which allows monitoring of the various stages of an automated test. The liquid actuator preferably comprises a liquid-filled bellows. On/off valves may comprise clip valves located in an elastomer hose, or e.g. of the ice valves of U.S. Pat. No. 5,311,896.

The reagent storage spaces included in the test unit are preferably bag-like foil kits as described in U.S. Pat. No. 4,588,554, which are compressible when emptied and do not require replacement air. Such kits require very small space in the test unit, and reagents will not be wasted with the use of these.

The test unit of the invention can be devised as a small-sized unit conducting specific tests automatically under a program within the range of the reagent selection included in the unit, which can be initiated by connection to a medium source, such as a water pipe. To conduct a test, all the user has to do is to introduce the sample to be tested into the test unit and to select the test to be conducted. Since the unit carries out the different steps of the test automatically, no special professional skill is required from the user.

In accordance with the invention, the separate test units described above can be combined to form a system, which is characterized by each test unit in the system being equipped for performing at least one test reaction in common for the different units, by the test units being operationally mutually independent, and by the test units being connected over data transmission communications to a common control unit, which emits signals allowing the control of the operation of the units.

U.S. Pat. No. 6,055,487, for instance, discloses a system known per se for clinical tests, where tests are conducted in a decentralized way at medical clinics or similar remote terminals under the control and surveillance of a common mainframe. In the system described in the reference, communication between the remote terminals and the mainframe can take place as telecommunications, for instance. However, the practical implementation of tests in the remote terminals is described as performed with conventional dosage robots, whose shortcomings are described in the background part of the present application. Although the reference claims as the advantage of the system that test results are rapidly obtained and still reliable, together with reduced need of education for those who perform the tests, the system still requires the remote terminals to be located at the medical clinics, health centers or laboratories, where professional staff experienced in test analyses is present.

By contrast, with the clinical test system based on test units with the hydraulic dosage of the invention, the simplicity and ease of use of the units for the first time enables users without professional education to perform the analyses. Line or wireless telecommunications are particularly suitable for contacts between individual test units acting as remote terminals and the common central control unit. The system of the invention is especially apt for use in remote districts or developing countries, where distances are long and communications and other infrastructure are deficient.

In the system of the invention, the individual test units may be very simplified and equipped only for conducting a few rare tests most in demand. In this situation, the test unit will need storage space only for a very limited range of reagents, required for carrying out these particular test reactions. The test unit is also provided with automation for conducting tests under programs stored in the unit. As mentioned above, all the user of the test unit has to do is to feed a sample into the inlet in the unit and select a program. The test result can be shown on a display included in the test unit or as a response from the control unit with which the test unit is communicating and which is in charge of correct results from the unit and checking and service functions with a view to maintain the efficiency of the unit.

In the system of the invention, individual test units with the reagents introduced in advance and the pre-programmed tests may be mutually identical or they may be tailored mutually differently to the different needs prevailing in different remote terminals. The needs may vary according to the geographical location of the test unit, and some units may contain reagents and programs for a larger number of tests than other units. Owing to the simple design of the test units, they can readily be transferred from one place to another whenever necessary, and a transferred unit is easily brought into working condition.

The scope of the invention especially covers the use of a test unit as described above or of a system composed of such units in diagnostic or similar clinical tests of medical specimens from a patient, such as blood or urinary samples, and also the use of the test unit or system in research, industrial or environmental testing.

Regardless of the facts above, the invention naturally also covers professional implementation of any other test unit, system of test units and method used in these within the scope of the claims below.

BRIEF DESCRIPTION OF THE DRAWINGS

The invention is explained more in detail below with the aid of an example and with reference to the accompanying drawing, in which.

BEST MODE FOR CARRYING OUT THE INVENTION

The embodiment example described here relates to a test system in clinical chemistry, which conducts diagnostic tests of liquid samples from a patient, such as blood or urinary samples. The system comprises a central control unit 1, which preferably communicates over wireless telecommunications 2 with a plurality of test units 3 remote relative to the control unit 1. The test units 3 acting as remote terminals in the system carry out practical tests under the control and surveillance of the central control unit 1.

Figure 1:
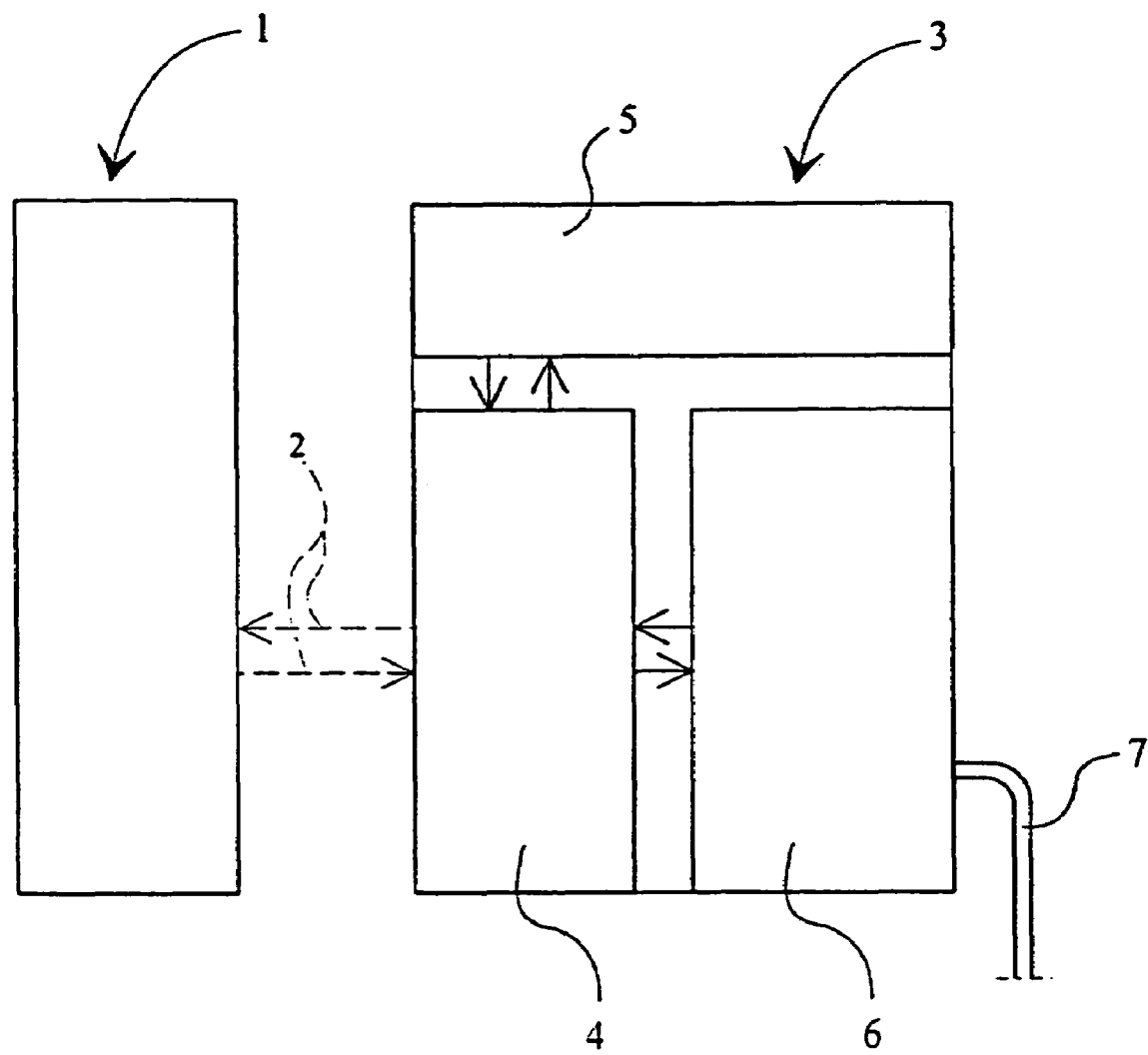
FIG. 1 is a block diagram of an individual test unit, which acts as a remote terminal in telecommunication with the central control unit.

The system may comprise several functionally independent test units 3, of which FIG. 1 in the drawing illustrates only one. The operational idea of the system is utilizing the computer capacity of its key central control unit 1 including its diagnostic software, patient records and service functions, in test units 3 acting as remote terminals, which are simple and easy to use, so that no special professional analyzing know-how is required from the users. The system avoids transport of medical specimens, provides notably more rapid test results and reliable results under the control of the control unit 1.

As shown in FIG. 1, a individual test unit 3 in the system comprises three blocks, i.e. a data control block 4, which is in charge of the control, data storage and telecommunication functions of the test unit, an interface 5 including a keyboard and a display, an a liquid treatment block 6, which carries out the actual test and comprises an inlet 7 for the sample to be tested, all of these three blocks being in telecommunication with the central control unit 1.

Figure 2:
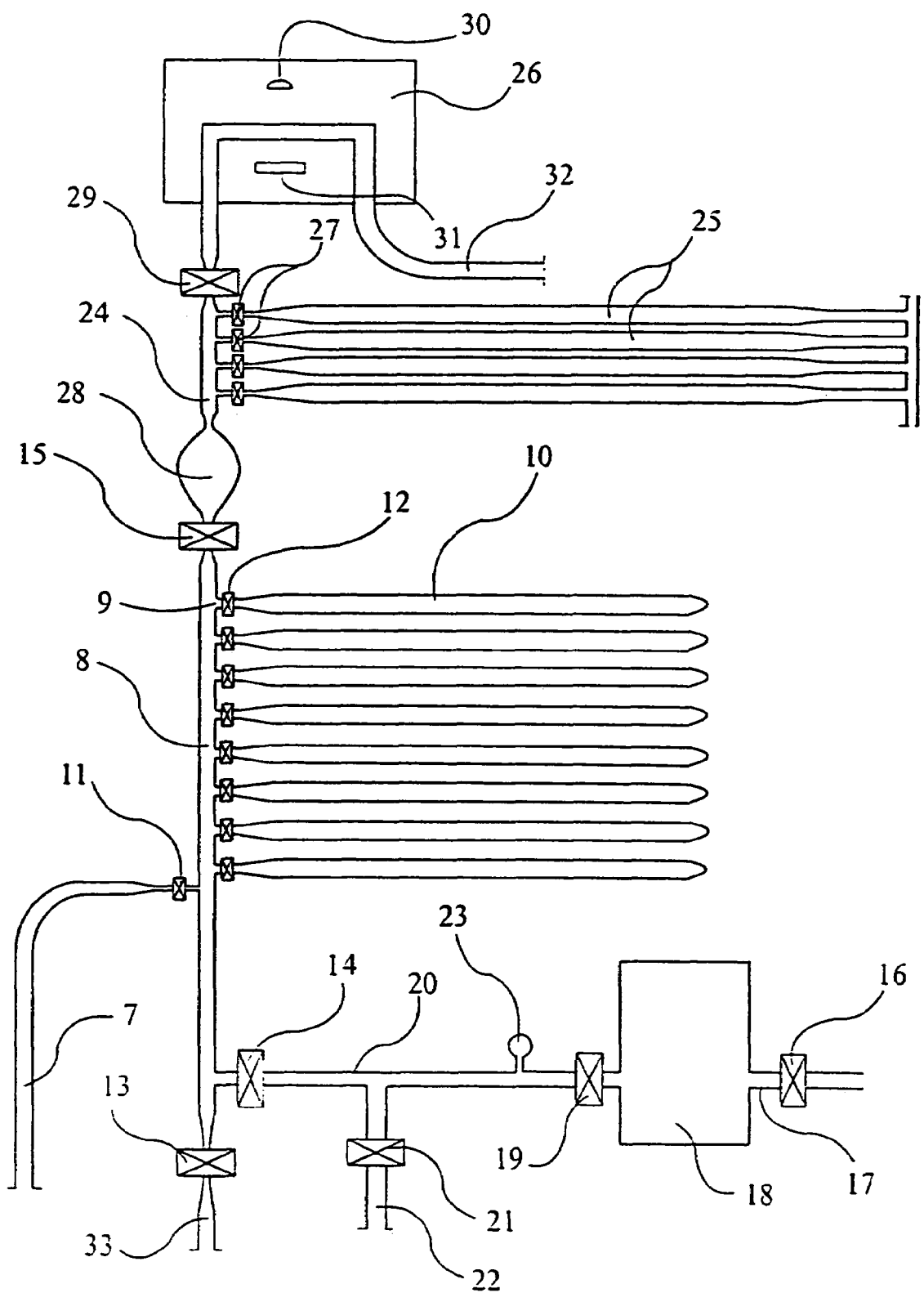
FIG. 2 is a more detailed view of the liquid treatment block included in the test unit, comprising a liquid space, flow channels and valves.

The liquid treatment block 6 of the test unit in FIG. 2 makes a diagnostic test of a liquid medical specimen by carrying out a test reaction and by detecting the end result of the reaction. The block 6 comprises an elongated, tubular dosage space 8, to which the needle-like suction duct 7 forming the sample inlet is connected. In addition, the dosage space 8 is connected with a plurality of reagent storage spaces 10 through parallel flow channels 9, the storage spaces comprising for instance bag-like compressible film kits. The reagents needed in the test reactions and control reactions to be performed with the test unit 3 are stored in these reagent bags 10. The feed duct 7 and each flow channel 9 for dosing reagents are equipped with an on/off valve 11, 12, and in addition, the dosage space 8 is defined by on/off valves 13, 14 and 15. The valves 11-15 thus determine the volume of the dosage space 8. For dilution of the sample to be tested and the reagents required for the test, the block 6 may use water as the medium, and for this purpose the block is connected to the water mains over a pipe 17 equipped with a valve 16. Water is supplied from the pipe 17 into a reciprocating bellows 18 acting as an actuator, which communicates over a duct 20 equipped with valves 14, 19 with the dosage space 8. The liquid treatment block 6 is devised so as to control liquid transfer in all the parts of the blocks with suction and expulsion movements generated by the bellows 18.

An air duct 22 equipped with a valve 21 is connected to said duct 20 between the dosage space 8 and the bellows 18. This allows the use of air as a buffer for the transfer of liquids from one part to the other of the block 6. The duct 20 is additionally equipped with a pressure sensor 23 acting as a sensor, allowing the monitoring of liquid movements generated with the bellows 18 in different parts of the block. The sensor 23 detects each starting, arrival to the valve location and stop of the liquid as a pressure variation in the duct system.

At the end opposite to the bellows 18 and to the water and air inlets 17, 22, the dosage space 8 ends in a valve 15, from where a duct 24 continues to the incubation spaces 25 and the detection space 26 formed of a measuring filter trough in the block 6. Adjacent incubation spaces 25 are separated from the duct 24 with on/off valves 27, and the reaction mixture, which is formed in the dosage space 8 and consists of the sample to be tested in these, one or more reagents and water acting as a medium can be conserved over the period required for the rest reaction at a regulated reaction temperature. For mixing associated liquids in the dosage space 8, the duct 24 comprises an expansion 28 acting as a mixing space. The aligned connections between the incubation spaces 25 are followed by an on/off valve 29 in the duct 24, preceding the measuring filter trough 26, which is equipped with a light source 30 and a detector 31. An outlet duct 32 continues from the measuring filter trough 26 for discharging the liquid used for the test from the block 6.

The parts of the block 6 used for dosage, test reaction and result detection need to be cleaned between the tests, and for this purpose the block is equipped with a detergent liquid inlet 33, which is connected to the dosage space 8 and separated from this with a valve 15. The detergent liquid can be discharged from the block into an outlet duct 32 starting from the measuring filter trough 26.

In the initial situation of the test to be conducted with the test unit 3, the liquid treatment block 6 is cleaned and dried, and the valves 12, 13 and 15 (cf. FIG. 2) defining the dosage space 8 are closed. The user of the unit connects the needle-like suction duct 7 acting as the sample inlet to the sample to be examined and starts the process. The bellows 18 then draws sample in the duct 7 all the way to the valve 11, and then the valve 11 is closed.

Next, the bellows 18 carries out filling of the dosage space 8 with water acting as a medium, supplied from the water pipe 17. The valve 15 after the dosage space 8 is opened, and the bellows 18 propels water through the duct 20 into the dosage space until the water reaches the opened valve 15. Water entering the valve gap entails a small change of pressure, which is recorded by the pressure sensor 23, and at that moment the automation closes the valve 15. As the filling starts, the valves 21 and 13 of the air and detergent liquid inlets 22, 33 are also open, so that water propelled by the bellows 18 fills these pipes all the way to the valves and the pressure sensor 23 causes the valves to be closed at the moment of filling. As a result of these operations, the dosage space 8 is hydraulically filled with water.

At the subsequent sample dosing stage, the valve 11 of the sample inlet 7 is opened, and the bellows 18 draws water from the dosage space 8, so that an amount of sample equalling the exhaust suction is drawn from the inlets 7 into the dosage space. This sample dosing stage ends when the valve I1 of the inlet 7 is closed.

Next, one or more reagents needed in the test is dosed accordingly into the dosage space 8. The valve 12 closing the film kit 10 containing the selected reagent is opened, and the bellows 18 draws water from the dosage space 8 so that an amount of reagent equalling the exhaust suction is drawn into the dosage space, after which the valve 12 is closed. If more than one reagent is needed, the dosage of the different reagents is carried out one by one with the operations described above. As a result, the dosed sample and the reagents are brought into the elongated, tubular dosage space 8 in succession, without notable mixing of the liquids at this stage. When the dosage is ended, the valve 14 of the dosage space 8 facing the bellows is closed and the duct 20 is purged of water by absorption with the bellows 18.

The following stage of the test comprises mixing of the dosed liquids and mutual reacting of the sample and the one or more reagents. To this end, the valve 15 after the dosage space 8 and the valve 27 connected with the selected incubation space 25 are opened, and the dosed liquids are expelled with the bellows from the space 8 into the mixing space 28, and in conjunction with this, the valve 21 of the inlet 22 is opened in order to use air as a buffer for the liquid transfers produced by the bellows. The liquids are mixed in the space 28 with reciprocating movements generated by the bellows, and part of the mixed liquid is further expelled with the bellows to the measuring filter trough 26 for determination of the initial value of measurement. The main portion of the liquid is propelled with the bellows into the incubation space 25 over the period needed for the test reaction to develop. While the reaction is taking place, the measuring filter trough 26 is cleaned with the detergent liquid supplied from the pipe 33, the detergent being propelled through the dosing and mixing spaces 8, 28 to the measuring filter trough and further to the outlet duct 32 by means of air supplied from the pipe 22. After the reaction, the reaction mixture is drawn from the incubation space 25 to the duct 24 between the dosage space and the measuring filter through and is expelled into the filter trough 26 for final measurement. After the measurement, the reaction mixture is expelled by air into the outlet duct 32.

The removal of the reaction mixture after the test from the liquid treatment block 6 may be integrated in the operation of cleaning the block between the tests. The detergent liquid is supplied from the pipe 33 and is driven by the bellows 18 with air conducted from the pipe 22 through the dosage space 8, the mixing space 28 and the measuring filter trough 26 to the outlet duct 32. Air flows in the center of the spaces and the ducts, and a very small amount of water is enough for cleaning in the form of an air-driven film along the walls of the spaces and the films. The sample inlet 7 is cleaned by opening the valve 11, so that air propelled by the bellows drives detergent liquid through the inlet 7 out from the liquid treatment block 6.

All of the liquid treatment operations described above take place under automatic control in the liquid treatment block 6 of the test unit, which is sealed from the environment with the exception of said inlet 7, 17, 22 and 33. The data control block 4 of the unit can show the test result directly on the display of the interface 5, or the result can be transmitted for processing in the central control unit 1, either by the user or by telephone or as automatic data transmission, for instance.

In the test unit 3 described above, all the dosages are hydraulic precision dosages owing to the repetition precision of the movements of the bellows 18, the dosages being ensured by means of the pressure sensor 23. The reagents contained in the reagent bags 10 are concentrated storage solutions, the data control unit 4 and the central control unit 1 being continuously informed of the remaining amounts of reagents. The test unit may be equipped with a cooler for maintaining the reagent bags 10 at refrigerator temperature, for instance. When purged, the reagent bags 10 collapse without requiring replacement air, and their uncontaminated conservation is ensured in the closed block. By means of automation, it can be continually ensured that a vacuum generated by the bellows 18 is prevailing continually while the valves 9 are open, so that the reagents are merely allowed to flow out from the bags into the dosage space, and never in the opposite direction.

The dosage space 8 of the liquid treatment block and the spaces and ducts where the reaction mixture formed by the liquids is treated have a stiff construction, being made e.g. of glass or metal pipe. The valves regulating the liquid transfers are advantageously carried out as clip valves made of Marprene elastomer, which have extremely high wear resistance. However, other valve solutions, as for instance ice valves closed by icing, are also conceivable.

Any operation errors or dysfunctions of the test unit caused by contamination of the ducts can be detected as a change of response by the pressure sensor 23. Thus, for instance, material accumulating on the walls of the dosage space 8 reduces the dosage volume, so that there is room for a smaller amount of liquid in the space, and when the space is being filled, the flow response of the valve 15 after the space occurs too soon. The data control unit 4 or central control unit 1 of the test unit may comprise a stored automatic service program, which, in this situation, performs cleaning of the space by means of a dissolving reagent included in the reagent record consisting of the reagent bags 10 of the unit. Similarly, the test unit can be programmed to perform control measurements as required under good laboratory practice between the tests of the samples to be examined. These automated service operations and control measurements allow the test unit to maintain its efficiency in long-term use without any other actions requiring special professional skill.

It is obvious to those skilled in the art that the embodiments of the invention are not confined to the example described in detail above, but may vary within the scope of the following claims.

The invention claimed is:

1. A method of combining liquids for testing a liquid sample, comprising:
   providing the liquid sample in a feed duct, the feed duct configured for connection to a dosage space via an inlet valve, wherein the dosage space comprises a liquid medium; and withdrawing an amount of the liquid medium from the dosage space with a suction action while keeping the inlet valve opened, and drawing an amount of the liquid sample into the dosage space to replace the amount of liquid medium withdrawn from the dosage space.

2. A method as defined in claim 1, wherein said providing comprises drawing the liquid sample into the feed duct up to the inlet valve by an actuator connected to the dosage space, said method further comprising:
   closing said inlet valve;
   filling the dosage space with the liquid medium; and
   opening said inlet valve, wherein said amount of the liquid sample is drawn into the dosage space and said amount of the liquid medium is withdrawn from the dosage space by means of the actuator.

3. A method as defined in claim 2, wherein the actuator comprises a bellows.

4. A method as defined in claim 1, wherein the inlet valve is closed after said withdrawing.

5. A method as defined in claim 4, wherein the dosage space is connected to a storage space, the storage space comprising a storage unit containing a liquid reagent, the storage unit configured for connection to the dosage space via a unit valve, said method further comprising:
- withdrawing a further amount of the liquid medium from the dosage space while keeping the unit valve opened, so as to draw an amount of the liquid reagent into the dosage space via the unit valve for replacing the further amount of liquid medium withdrawn from the dosage space.

6. A method as defined in claim 5, wherein the storage space further comprising a plurality of further storage units containing further liquid reagents, the further storage units configured for connection to the dosage space via a plurality of further valves, and wherein the dosage space comprises an elongated duct having a first end connected to the actuator and a second end, the elongated duct configured for connection to the inlet valve, the unit valve and the further valves at different locations, so as to draw the liquid sample, the liquid reagent and one or more further liquid reagents into the dosage space in succession by the suction action of the actuator.

7. A method as defined in claim 5, wherein the dosage space comprises an elongated duct having a first end connected to the actuator and a second end, the second end, the elongated duct configured for connection to the inlet valve and the unit valve at different locations.

8. A method as defined in claim 7, wherein the second end of the duct is connected to a mixing space, said method further comprising:
- drawing a gaseous medium into the dosage space at the first end of the duct; and
- expelling contents in the duct into the mixing space using the gaseous medium as buffer, wherein the contents comprise the liquid sample, the liquid reagent and the liquid medium.

9. A method as defined in claim 8, further comprising:
- mixing the contents in the mixing space with reciprocating movements generated by the actuator.

10. A method as defined in claim 5, further comprising:
- transferring contents in the dosage space into an incubation space for allowing a reaction between the liquid sample and the liquid reagent to take place in order to determine a test result.

11. A method as defined in claim 5, wherein the dosage space is operatively connected to a sensor for monitoring liquid movements in the dosage space.

12. A method as defined in claim 1, wherein the liquid medium comprises water and the liquid sample comprises a liquid medical specimen.

* * * * *

UNITED STATES PATENT AND TRADEMARK OFFICE
CERTIFICATE OF CORRECTION

PATENT NO.       : 7,608,464 B2  Page 1 of 1
APPLICATION NO. : 10/467022
DATED            : October 27, 2009
INVENTOR(S)      : Kaartinen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1667 days.

Signed and Sealed this

Twelfth Day of October, 2010

David J. Kappos
*Director of the United States Patent and Trademark Office*